United States Patent
Hoglund et al.

(10) Patent No.: US 10,657,224 B2
(45) Date of Patent: May 19, 2020

(54) MONITORING AND TREATMENT DOSAGE PREDICTION SYSTEM

(71) Applicant: Accenture Global Solutions Limited, Dublin (IE)

(72) Inventors: Jonas Hoglund, Älvsjö (SE); Henrik Johansson, Stockholm (SE); Primrose Mbanefo, Newmarket (GB); Matthew O'Kane, London (GB)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 15/171,813

(22) Filed: Jun. 2, 2016

(65) Prior Publication Data

US 2017/0091419 A1    Mar. 30, 2017

Related U.S. Application Data

(60) Provisional application No. 62/232,795, filed on Sep. 25, 2015.

(51) Int. Cl.
*G16H 10/60* (2018.01)
*G16H 50/50* (2018.01)
(Continued)

(52) U.S. Cl.
CPC ......... *G06F 19/3468* (2013.01); *G16H 10/60* (2018.01); *G16H 20/30* (2018.01);
(Continued)

(58) Field of Classification Search
CPC ........ G06Q 10/00; G06Q 50/00; G16H 10/00; G16H 15/00; G16H 20/00; G16H 30/00;
(Continued)

(56) References Cited

U.S. PATENT DOCUMENTS 8,221,345 B2    7/2012   Blomquist
8,303,500 B2   11/2012   Raheman
(Continued)

FOREIGN PATENT DOCUMENTS

EP          1369688        12/2003
WO    WO 2013/097934 A1    7/2013

OTHER PUBLICATIONS

Niu, "1 Red Flag That Fitbit, Inc. Investors Can't Ignore," http://www.fool.com/investing/general/2015/06/24/1-red-flag-that-fitbit-inc-investors-cant-ignore.aspx, Jun. 2015, 5 pages.
(Continued)

*Primary Examiner* — Robert W Morgan
*Assistant Examiner* — Charles P Coleman
(74) *Attorney, Agent, or Firm* — Harrity & Harrity, LLP (57) ABSTRACT

A device may receive lifestyle information corresponding to an individual with a medical condition. The device may create a lifestyle timeline, associated with the individual, that includes a plurality of items of lifestyle information, included in the lifestyle information, arranged in a chronological order. The device may generate, based on the lifestyle timeline, a recommendation or a prediction associated with a metric related to the medical condition. The recommendation may be generated based on one or more of the plurality of items of lifestyle information. The prediction may be generated using a prediction model that uses one or more of the plurality of items of lifestyle information as input, and generates the prediction using the prediction model. The device may provide information associated with the recommendation or the prediction to identify a dosage associated with treating or managing the medical condition.

20 Claims, 5 Drawing Sheets

(51) Int. Cl.
*G16H 20/60* (2018.01)
*G16H 50/20* (2018.01)
*G16H 20/70* (2018.01)
*G16H 20/30* (2018.01)
*G06F 19/00* (2018.01)

(52) U.S. Cl.
CPC ............ *G16H 20/60* (2018.01); *G16H 20/70* (2018.01); *G16H 50/20* (2018.01); *G16H 50/50* (2018.01)

(58) Field of Classification Search
CPC ........ G16H 40/00; G16H 50/00; G16H 70/00; G16H 80/00; G16H 10/40; G16H 20/10; G16H 20/13; G16H 20/17; G16H 50/50; G16H 10/60; G06F 19/3468
USPC .................................................. 705/2, 3, 20
See application file for complete search history.

(56) References Cited

U.S. PATENT DOCUMENTS

| | | | |
|---|---|---|---|
| 8,762,306 B2 | 6/2014 | Cameron et al. | |
| 2002/0035316 A1* | 3/2002 | Drazen | G06F 19/3431 600/300 |
| 2002/0120471 A1* | 8/2002 | Drazen | G06F 19/322 705/3 |
| 2006/0025931 A1* | 2/2006 | Rosen | G06F 19/345 702/19 |
| 2006/0173663 A1* | 8/2006 | Langheier | G06F 19/3437 703/11 |
| 2008/0220403 A1* | 9/2008 | Marling | G06F 19/3481 434/262 |
| 2009/0006129 A1* | 1/2009 | Thukral | G06F 19/3437 705/2 |
| 2009/0198516 A1* | 8/2009 | Greenholtz | G06Q 10/00 705/3 |
| 2010/0047745 A1* | 2/2010 | Bergqwist | A61B 5/14532 434/127 |
| 2010/0161347 A1* | 6/2010 | Heath | G06F 19/3437 705/2 |
| 2010/0331651 A1 | 12/2010 | Groll | |
| 2011/0218435 A1 | 9/2011 | Srinivasan et al. | |
| 2011/0225112 A1* | 9/2011 | Cameron | G06F 19/3437 706/20 |
| 2012/0095313 A1* | 4/2012 | Reinke | G06Q 50/22 600/365 |
| 2012/0266251 A1* | 10/2012 | Birtwhistle | G06F 19/323 726/26 |
| 2013/0110549 A1 | 5/2013 | Hoglund et al. | |
| 2014/0019396 A1* | 1/2014 | Carlsgaard | G06N 5/02 706/46 |
| 2014/0046160 A1 | 2/2014 | Terashima | |
| 2014/0089836 A1 | 3/2014 | Damani et al. | |
| 2014/0156308 A1* | 6/2014 | Ohnemus | G06F 19/3418 705/3 |
| 2014/0164012 A1* | 6/2014 | Guillama | G06F 19/3437 705/2 |
| 2014/0288493 A1 | 9/2014 | Kamen | |
| 2014/0304204 A1* | 10/2014 | Cameron | G06F 19/3437 706/21 |
| 2014/0310294 A1 | 10/2014 | Stivoric et al. | |
| 2014/0324445 A1* | 10/2014 | Carlsgaard | G06Q 10/10 705/2 |
| 2014/0349257 A1 | 11/2014 | Connor | |
| 2015/0025394 A1 | 1/2015 | Hong et al. | |
| 2015/0046828 A1* | 2/2015 | Desai | G06F 1/163 715/739 |
| 2015/0178470 A1* | 6/2015 | Cederlund | G06F 19/363 705/2 |
| 2015/0193597 A1* | 7/2015 | Cederlund | G06F 19/363 705/2 |
| 2015/0227710 A1* | 8/2015 | Pappada | G06Q 50/22 705/2 |
| 2015/0242586 A1* | 8/2015 | Kagen | G06F 19/3431 705/2 |
| 2015/0364057 A1* | 12/2015 | Catani | G09B 19/0092 434/127 |
| 2016/0147976 A1* | 5/2016 | Jain | A61J 1/035 705/2 |

OTHER PUBLICATIONS

Chang et al. "Welcome to the Wellness Revolution: Old-school Wisdom meets Cutting-edge Tech," http://blog.mayfield.com/welcome-to-the-wellness-revolution-old-school-wisdom-meets-cutting-edge-tech/, Oct. 2015, 6 pages.

Mehregany, "How Can Wireless Health Get the Most Out of Wearables and Sensors?," http://www.designnews.com/author.asp?section_id=1386&doc_id=278616, Sep. 2015, 5 pages.

Gandhi, "Deconstructing the Fitbit IPO and S-1," https://rockhealth.com/deconstructing-fitbit-s-1/, May 2015, 9 pages.

Cipriani, "Here's why Fitbit is giving Target 335,000 fitness-tracking devices," http://fortune.com/2015/09/16/fitbit-hipaa/, Sep. 2015, 3 pages.

Saint Louis, "Many Schools Failing on Type 1 Diabetes Care," http://www.nytimes.com/2015/10/27/health/many-schools-failing-on-diabetes-care.html?_r=1, Oct. 2015, 4 pages.

ReportBuyer, "Global Wearable Medical Device Market—Growth, Trends and Forecasts (2015-2020)," http://www.prnewswire.com/news-releases/global-wearable-medical-device-market---growth-trends-and-forecasts-2015-2020-300170722.html, Nov. 2015, 6 pages.

Validic, "The Digital Health Trends Poised to Transform Healthcare in 2015," https://validic.com/wp-content/uploads/2015/04/2015-Digital-Health-Trends.pdf, Apr. 2015, 5 pages.

Mordor Intelligence, "Global Wearable Medical Devices Market—Growth, Trends and Forecasts (2015-2020)," http://www.mordorintelligence.com/industry-reports/global-wearable-medical-device-market-industry, Jun. 2016, 7 pages.

Stephan, "How FitBit-type gadgets could tie to worker's comp," http://www.cpbj.com/article/20150306/FACEFORWARD13/150309858/how-fitbittype-gadgets-could-tie-to-workers-comp, Mar. 2015, 3 pages.

Khan, "Can a Fitness Tracker Save You Money on Health Insurance?," http://health.usnews.com/health-news/health-wellness/articles/2014/10/03/can-a-fitness-tracker-save-you-money-on-health-insurance, Oct. 2014, 4 pages.

Barry, "Novartis-Qualcomm deal leads race to bring wearable tech to pharma," http://www.outsourcing-pharma.com/Clinical-Development/Novartis-Qualcomm-deal-leads-race-to-bring-wearable-tech-to-pharma, Jan. 19, 2015, 3 pages.

Rubin, "Your Trainer Saw That: Devices Like Fitbit and Up24 Being Used by Gyms to Track Clients' Activity," http://www.nytimes.com/2014/04/17/fashion/devices-like-fitbit-and-up24-being-used-by-gyms-to-track-clients-fitness-activity.html, Apr. 2014, 5 pages.

Yu, "Samsung reportedly looking for partners to put healthcare tech into wearables," http://www.zdnet.com/article/samsung-reportedly-looking-for-partners-to-put-healthcare-tech-into-wearables/, Nov. 2014, 11 pages.

White House, "Fact Sheet: Obama Administration Announces New Flexible Hybrid Electronics Manufacturing Innovation Hub in San Jose, CA," https://www.whitehouse.gov/the-press-office/2015/08/28/fact-sheet-obama-administration-announces-new-flexible-hybrid, Aug. 2015, 8 pages.

Comstock, "Google X is developing a wearable for clinical research," http://mobihealthnews.com/44622/google-x-is-developing-a-wearable-for-clinical-research, Jun. 2015, 14 pages.

Databetes, "Meal Memory," www.databetes.com, Jan 4, 2016, 2 pages.

Wikipedia, "Glooko," https://en.wikipedia.org/wiki/Glooko, Apr. 29, 2016, 3 pages.

Tenderich, "New Livongo Plugs Glucose Testing into Real-Time Care, Research," http://www.healthline.com/diabetesmine/new-livongo-connects-glucose-testing, Sep. 17, 2014, 12 pages.

(56) References Cited

OTHER PUBLICATIONS

MyNetDiary, "To lose weight and stay healthy for life you need a food and exercise diary. MyNetDiary makes it easy," http://www.mynetdiary.com/, Sep. 25, 2010, 14 pages.
MySugr, "mySugr Logbook," https://mysugr.com/apps/, Apr. 8, 2016, 5 pages.
PredictBGL, "ManageBGL Features," http://predictbgl.com/features.html, Apr. 20, 2015, 4 pages.
Rimidi, "Rimidi—Serious Hope for Healthcare," http://www.rimidi.com/solution/, Nov. 10, 2015, 8 pages.
Tidepool, "Blip: The hub for your diabetes data," http://tidepool.org/products/blip/, Jan. 16, 2016, 5 pages.
Moment, "WellDoc DiabetesManager," http://www.momentdesign.com/what-we-do/case-studies/welldoc-diabetesmanager, Feb. 12, 2013, 2 pages.
European Commission, "EUBIROD—A European diabetes database," http://ec.europa.eu/health/highlights/2012/13/short_content_en.htm, May 12, 2016, 2 pages.
Health Consumer Powerhouse, "Euro Diabetes Index," http://www.healthpowerhouse.com/index.php?option=com_content&view=category&layout=blog&id=46&Itemid=66, Sep. 17, 2014, 2 pages.
Fitbit, Inc., "Fitbit—Class a Common Stock", Nov. 9, 2015, 256 pages.
European Search Report corresponding to EP 16 18 9847, dated Jan. 25, 2017, 9 pages.
"Introducing Convenient Mobile Access to Your Pump and CGM Data With Minimed Connect", posted by Editorial Team, published on Jun. 4, 2015, [online article], [retrieved from the Internet on Oct. 23, 2017], <URL: https://www.medtronicdiabetes.com/loop-blog/introducing-convenient-mobile-access-pump-cgm-data-minimed-connect/>.
"Medtronic's MiniMed Connect—Sending Pump/CGM Data to Smartphones", published on Jun. 6, 2015, [online article], [retrieved from the Internet on Oct. 23, 2017], <URL: https://diatribe.org/medtronic-minimed-connect-sending-pumpcgm-data-smartphones>.

\* cited by examiner

MONITORING AND TREATMENT DOSAGE PREDICTION SYSTEM

RELATED APPLICATION

This application claims priority under 35 U.S.C. § 119 to U.S. Provisional Patent Application No. 62/232,795, filed on Sep. 25, 2015, the content of which is incorporated by reference herein in its entirety.

BACKGROUND

An individual with a treatable and/or a manageable medical condition, such as diabetes, may manage the medical condition by periodically administering treatment (e.g., the consumption of food or the administration of medication such as insulin or glucagon). The type and dosage of medication may be based on monitoring the individual's health metrics (e.g., blood glucose levels) and/or other information that may affect the type and dosage of medication to be administered for treating the medical condition. For example, diabetic individuals may experience hypoglycemia (e.g., a condition in which blood glucose levels are lower than a target or optimal level) or hyperglycemia (e.g., a condition in which blood glucose levels are higher than a target or optimal level). Hypoglycemia may be treated by the consumption of glucose via supplements or food. In extreme cases, hypoglycemia may also be treated via medication, such as glucagon injections. Hyperglycemia may be treated by insulin injections. Also, diabetic individuals may treat or manage diabetes using various dosages and types of insulin (e.g., rapid-acting insulin, slow-acting insulin, etc.). Diabetic individuals may utilize insulin pumps that may continuously provide insulin at a particular rate, or may provide a burst of insulin when needed (e.g., after the consumption of food).

SUMMARY

According to some possible implementations, a method may include: receiving, by a device, lifestyle information corresponding to an individual with a medical condition; creating, by the device and based on the lifestyle information, a lifestyle timeline associated with the individual, where the lifestyle timeline may include a plurality of items of lifestyle information, included in the lifestyle information, and where the lifestyle time line may have the plurality of items of lifestyle information arranged in a chronological order; generating, by the device and based on the lifestyle timeline, a recommendation or a prediction associated with a metric related to the medical condition, where the recommendation may be generated based on one or more of the plurality of items of lifestyle information, or where the prediction may be generated using a prediction model that uses one or more of the plurality of items of lifestyle information as input, and generates the prediction using the prediction model; and providing, by the device, information associated with the recommendation or the prediction, where the information associated with the recommendation or the prediction may be provided to identify a dosage associated with treating or managing the medical condition, where the dosage may be identified based on the recommendation or the prediction.

According to some possible implementations, a device may include one or more processors to: receive lifestyle information corresponding to an individual with a medical problem; create, based on the lifestyle information, a lifestyle timeline associated with the individual, where the lifestyle timeline may include a plurality of items of lifestyle information included in the lifestyle information, and where the lifestyle timeline may have the plurality of items of lifestyle information arranged in a chronological order; generate, based on the lifestyle timeline, a recommendation or a prediction associated with a health metric related to the medical problem, where the recommendation may include a recommended dosage of a treatment associated with the health metric and being generated based on one or more of the plurality of items of lifestyle information, or where the prediction may include a predicted value of the health metric at a future time and being generated by a prediction model that uses one or more items of the plurality of lifestyle information as input; and provide, for display to the individual, information associated with the recommendation or the prediction, where the information associated with the recommendation may be provided to identify the recommended dosage, or where the information associated with the prediction may be provided to identify the predicted value of the health metric.

According to some possible implementations, a non-transitory computer-readable medium may store one or more instructions that, when executed by one or more processors, cause the one or more processors to: receive lifestyle information corresponding to an individual with a medical problem; create, based on the lifestyle information, a lifestyle timeline associated with the individual, where the lifestyle timeline may include a plurality of items of lifestyle information included in the lifestyle information, and may have the plurality of items of lifestyle information arranged in a chronological order; determine, based on the lifestyle information, a current value of a metric associated with the medical problem; generate, based on the lifestyle timeline and the current value of the metric, a recommendation or a prediction associated with the metric, where the recommendation may be generated based on a first set of the plurality of items of lifestyle information, or where the prediction may be generated using a predictive model that uses a second set of the plurality of items of lifestyle information as input, and generates the prediction using the predictive model; and provide information associated with the recommendation or the prediction, where the information associated with the recommendation or the prediction may be provided to identify a dosage, associated with the medical problem, or the prediction associated with the metric.

DETAILED DESCRIPTION

The following detailed description of example implementations refers to the accompanying drawings. The same reference numbers in different drawings may identify the same or similar elements.

An individual with a medical problem (e.g., a disease, a disorder, a condition, etc.) may need to monitor and/or manage the medical problem by administering (e.g., ingesting, injecting, applying, etc.) a dosage of a treatment (e.g., medication). For example, an individual afflicted with diabetes (e.g., type 1 or type 2 diabetes) may monitor and/or manage the condition by measuring blood glucose levels one or more times a day. Based on the blood glucose levels and/or a predicted trend of blood glucose levels, the individual may administer certain treatment. For example, in the case of hyperglycemia the individual may administer insulin. In the case of hypoglycemia, the individual my consume glucose or administer other medication (e.g., glucagon).

Monitoring and/or managing such a medical problem may be difficult since dosages of the treatment may vary widely (e.g., from hour to hour, from day to day, etc.) based on a multitude of factors associated with the individual. In the case of diabetes, for example, a trend in blood glucose levels of the diabetic individual may vary widely based on the individual's diet, the individual's activity level, previous dosages of insulin, biological factors associated with the individual, environmental conditions associated with the individual, or the like. Here, dosages of insulin or glucose consumption may be difficult to forecast and/or predict due to a trend in glucose levels being affected by the multitude of factors. As such, the monitoring and/or managing of the medical problem may require constant and close attention by the individual (or those charged with the individual's care). For example, insufficient insulin (e.g., for treating hyperglycemia) may cause the individual to remain hyperglycemic, and excess insulin may cause the individual to become hypoglycemic. Similarly, insufficient glucose consumption (e.g., for treating hypoglycemia) may cause the individual to remain hypoglycemic, whereas excess glucose consumption may cause the individual to become hyperglycemic.

Implementations described herein may provide a computer-implemented monitoring and treatment dosage prediction system that is capable of determining lifestyle information associated with an individual. Further, implementations described herein may analyze the lifestyle information (e.g., to identify patterns, correlations, trends, etc.) associated with the individual, and provide the individual with a recommended dosage of the treatment (e.g., an immediate dosage of the treatment, a future dosage of the treatment, etc.). Additionally, or alternatively, implementations described herein may predict other conditions associated with the medical problem (e.g., a predicted change or trend in a blood glucose level). Accordingly, the recommended dosage of the treatment for an individual may take into consideration the individual's lifestyle information in order for the individual to better manage a medical problem (e.g., diabetes).

Further, the implementations described here allow processing resources, memory resources, and/or battery life of one or more user devices, associated with the individual, to be conserved (e.g., since the one or more user devices are not required to store the lifestyle information, analyze the lifestyle information, create the lifestyle timeline, and/or generate the recommendation and/or prediction).

Figure 1A:
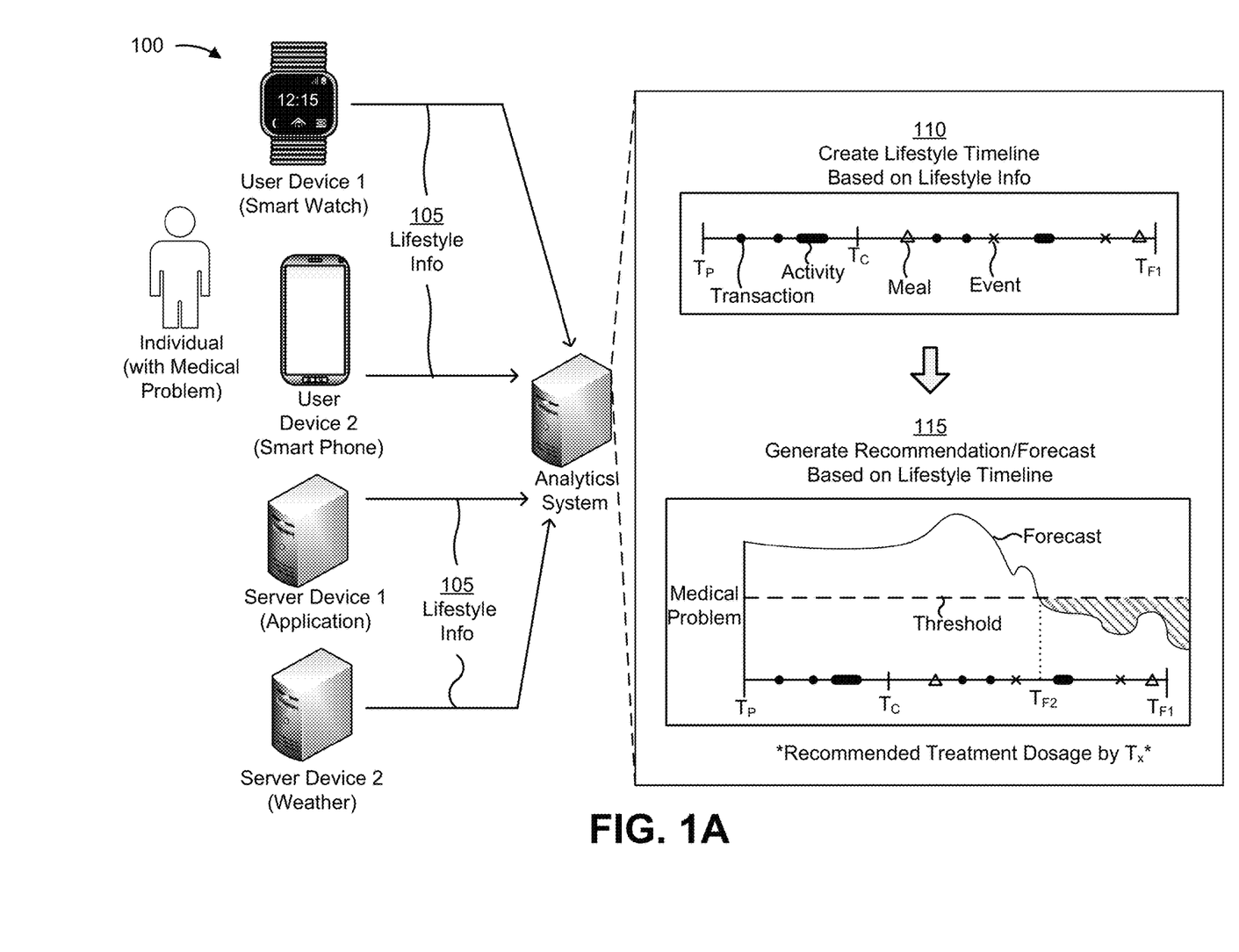
FIGS. 1A and 1B are diagrams of an overview of an example implementation described herein.
Figure 1B:
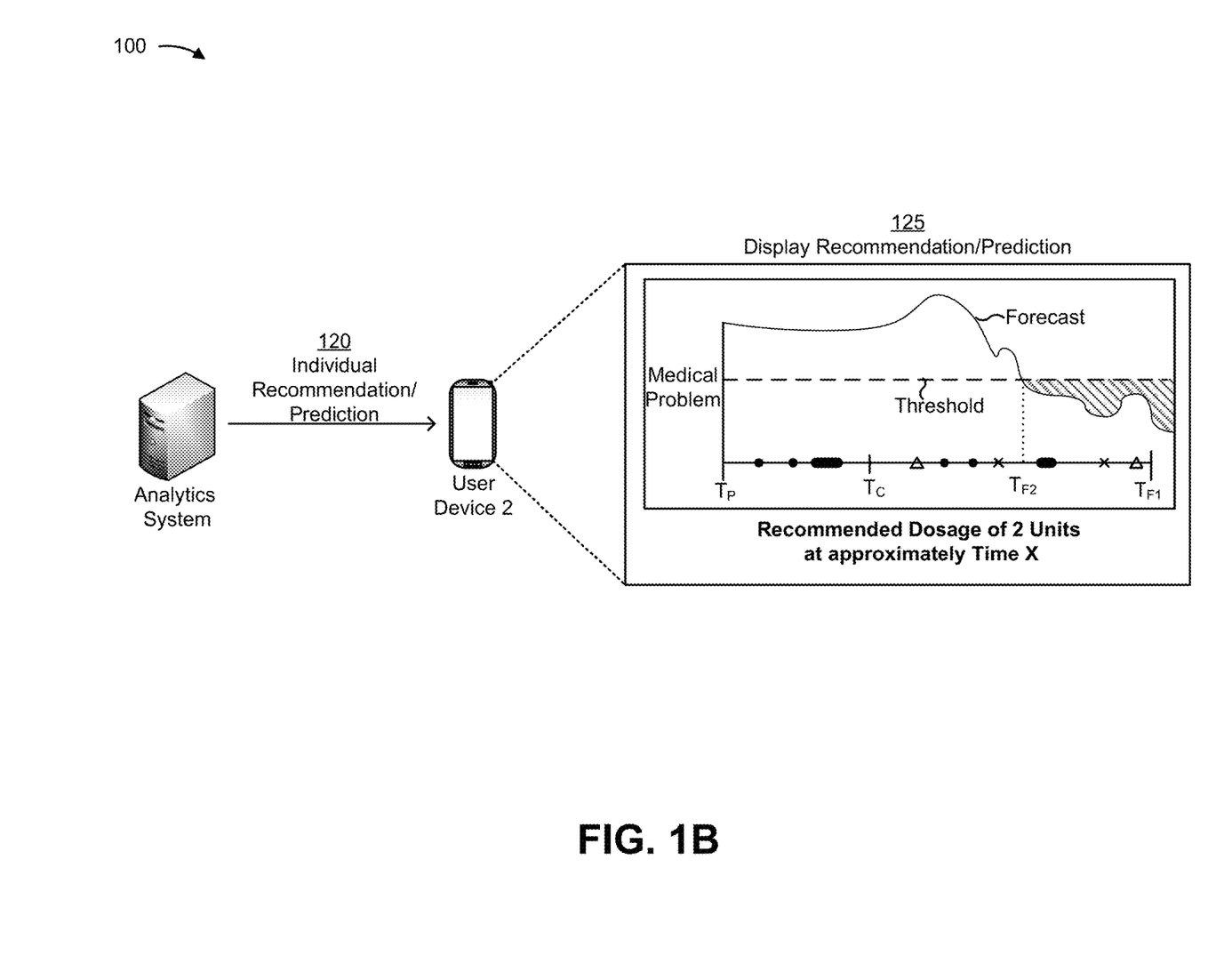

FIGS. 1A and 1B are diagrams of an overview of an example implementation 100 described herein. As shown by reference numeral 105 in FIG. 1A, an analytics system may receive a variety of lifestyle information associated with an individual (e.g., information specific to the individual, general information that may add context to another item of lifestyle information associated with the individual) that suffers from a medical problem (e.g., diabetes). For example, the analytics system may receive the lifestyle information from various sources, such as a user device (e.g., user device 1 which may include a smart watch, a smart phone, a fitness band, a continuous glucose monitor (CGM), and/or the like). Additionally, or alternatively, the analytics system may receive the lifestyle information from an application server that hosts an application executed on user device 2 associated with the individual. Here, the lifestyle information, provided by the application server, may be specific to the individual. Additionally, or alternatively, the analytics system may receive the lifestyle information from a weather data server that has access to general weather data. Here, the lifestyle information, provided by the weather data server, may be general information and/or contextual information. As described herein, the lifestyle information may include information that may be used to predict or identify a trend in the individual's vital signs and/or other health metrics (e.g., blood glucose levels). In some implementations, the lifestyle information may include items, such as financial transactions, activities, meals, events, stress levels, heart rate, sleep patterns, and/or other information regarding the individual that may be used to forecast or identify a trend in the individual's health metrics (e.g., blood glucose levels).

In other words, in some implementations, the lifestyle information may be associated with the individual. Additionally, or alternatively, the lifestyle information may include general information and/or contextual information that may be used to add context to one or more other items of lifestyle information. For example, the lifestyle information may include weather data, geo-spatial information system data, and/or another type general information and/or contextual information that is not specific to the individual.

The analytics system may generate a recommendation and/or a prediction, associated with the medical problem (e.g., a predicted trend of blood glucose levels, a predicted value associated with a health metric) based on the lifestyle information. For example, as shown by reference numeral 110, the analytics system may create a timeline, associated with the individual, based on the lifestyle information. The timeline may identify the lifestyle items during a time period from a past time (Tp) to a current time (Tc) and until a first future time (TF1).

As shown by reference number 115, the analytics system may use predictive factors to generate a recommendation associated with monitoring and/or managing the medical problem (e.g., an amount of insulin or glucagon to inject, an amount of glucose to consume), and another future time at which to administer the injection or consume the glucose (e.g., identified as time F2 (TF2) in FIG. 1A). Additionally, or alternatively, the analytics system may determine a prediction associated with the medical problem. For example, the analytics system may predict or forecast a metric (e.g., blood glucose level) of the individual (e.g., as shown by a forecast line in FIG. 1A). In some implementations, the analytics system may identify a target or threshold value for the metric. As described herein, the threshold value may be used to determine a recommendation for treating or managing the individual's medical condition (e.g., a recommended dosage of insulin or glucose consumption). In some implementations, the glucose levels prior to the current time Tc may be based on actual glucose levels (e.g., as measured by a CGM), and the glucose levels after the current time Tc may be forecasted levels that are determined based on the lifestyle timeline.

As shown by reference numeral 120 in FIG. 1B, the analytics system may provide the individual's recommendation/prediction to a user device (e.g., user device 2). As shown by reference number 125, the user device may display the recommendation/prediction in the form of a graph. For example, the user device may display the lifestyle timeline, the forecasted health metrics (e.g., glucose levels), and a recommendation for treatment of the medical condition (e.g., diabetes) at a particular time. In the example of FIG. 1B, the user device may display a recommended dosage of 2 units at approximately time TF2.

In some implementations, the forecasted health metrics may be based on a determination that the individual failed to follow the recommended dosage. In the example of FIG. 1B, neglecting to treat the medical problem in accordance with the recommendation may cause the glucose levels to drop below a particular target or threshold (e.g., thereby resulting in hypoglycemia). Here, the forecasted glucose level at time TF1 may identify a forecasted glucose level at time TF1 if the recommended dosage is not administered at time TF2. Accordingly, the recommendation may include a recommended dosage for the consumption of glucose at a particular time. In some implementations, the forecasted health metrics may be based on a determination that the individual followed the recommended dosage (i.e., was compliant with a treatment protocol), in which case the forecasted health metrics is within an acceptable margin of error with respect to the target or threshold.

As described herein, lifestyle information for an individual with a medical problem (e.g., diabetes) may be used to forecast a trend in the individual's health metrics (e.g., glucose levels). Further, recommended dosages for managing and treating the individual's medical problem may be determined based on the determined trend and the individual's lifestyle information. As a result, the individual may better manage and treat the medical condition since recommended dosages take into consideration the user's lifestyle information, including the user's future activities, planned meals, etc. which may affect the user's health metrics.

As indicated above, FIGS. 1A and 1B are provided merely as an example. Other examples are possible and may differ from what was described with regard to FIGS. 1A and 1B.

Figure 2:
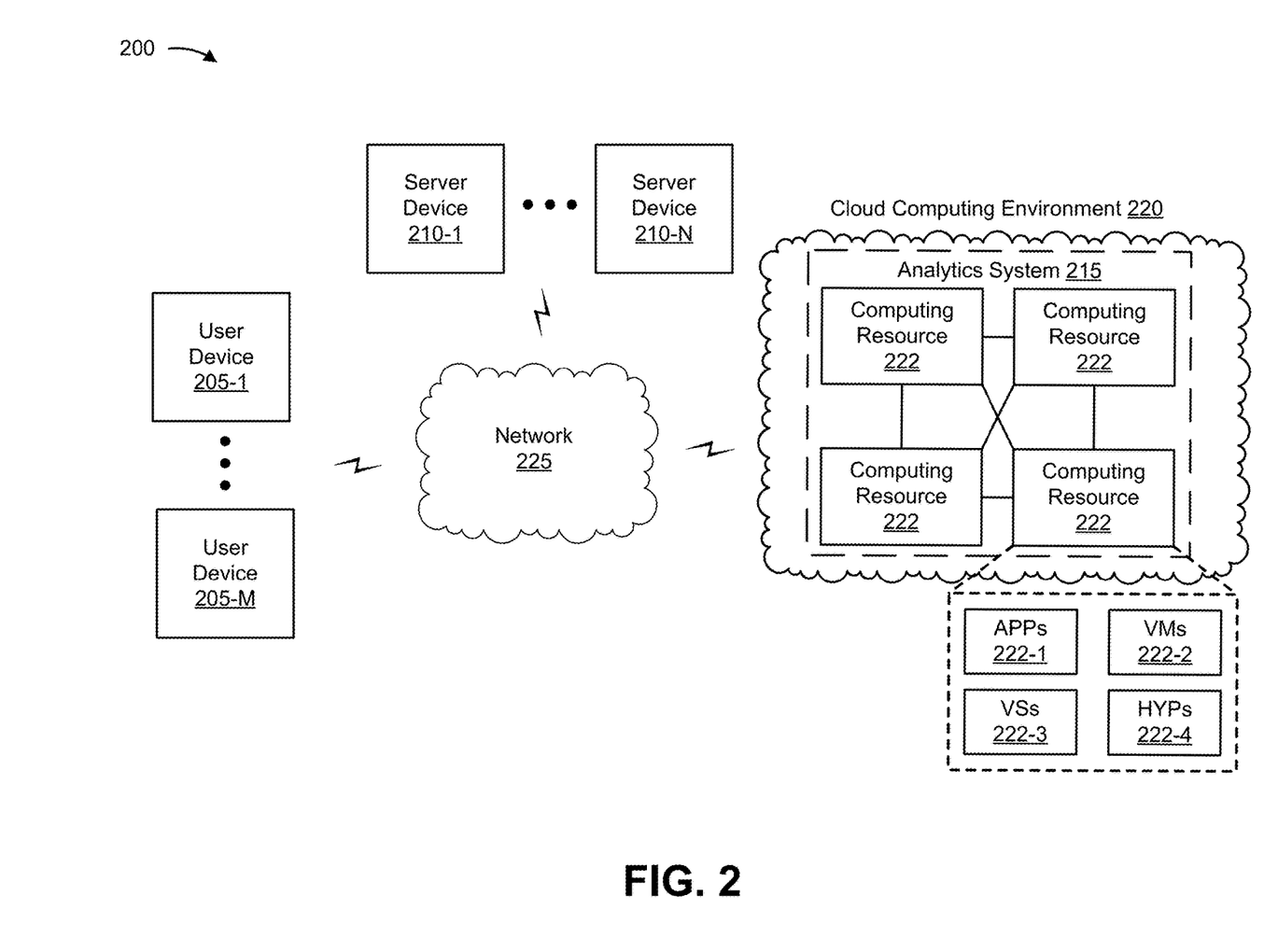
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include one or more user devices 205-1 through 205-M (M≥1) (hereinafter referred to collectively as "user devices 205," and individually as "user device 205"), one or more server devices 210-1 through 210-N (N≥1) (hereinafter referred to collectively as "server devices 210," and individually as "server device 210"), an analytics system 215 hosted within a cloud computing environment 220, and a network 225. Devices of environment 200 may interconnect via wired connections, wireless connections, or a combination of wired and wireless connections.

User device 205 includes one or more devices capable receiving, storing, and/or providing, to an individual, information associated with a prediction and/or a recommendation associated with a dosage of a treatment for a medical problem. For example, user device 205 may include a communication and/or computing device, such as a mobile phone (e.g., a smart phone, a radiotelephone, etc.), a laptop computer, a tablet computer, a handheld computer, a gaming device, a wearable communication device (e.g., a fitness band, a smart wristwatch, a pair of smart eyeglasses, a sensor, a CGM, an insulin pump, etc.), or a similar type of device. In some implementations, user device 205 may be capable of receiving, collecting, generating, processing, and/or providing lifestyle information associated with the individual.

Server device 210 includes one or more devices capable of receiving, storing, and/or providing lifestyle information associated with an individual. For example, server device 210 may include a server or a group of servers. In some implementations, server device 210 may host an application associated with the lifestyle information and/or may store the lifestyle information (e.g., such that server device 210 may provide the lifestyle information to analytics system 215).

Analytics system 215 includes one or more devices capable of determining lifestyle information associated with an individual, analyzing the lifestyle information associated with the individual, and/or providing the individual with a prediction and/or a recommendation for a dosage of a treatment. For example, analytics system 215 may include a server or a collection of servers. In some implementations, analytics system 215 may be capable of storing, accessing, creating, training, updating, and/or modifying a prediction model associated with determining the recommendation for the dosage of the treatment.

In some implementations, as shown, analytics system 215 may be hosted in cloud computing environment 220. Notably, while implementations described herein describe analytics system 215 as being hosted in cloud computing environment 220, in some implementations, analytics system 215 may not be cloud-based (i.e., may be implemented outside of a cloud computing environment) or may be partially cloud-based.

Cloud computing environment 220 includes an environment that hosts analytics system 215. Cloud computing environment 220 may provide computation, software, data access, storage, etc. services that do not require end-user (e.g., user device 205) knowledge of a physical location and configuration of system(s) and/or device(s) that hosts analytics system 215. As shown, cloud computing environment 220 may include a group of computing resources 222 (referred to collectively as "computing resources 222" and individually as "computing resource 222").

Computing resource 222 may include one or more personal computers, workstation computers, server devices, or another type of computation and/or communication device. In some implementations, computing resource 222 may host analytics system 215. The cloud resources may include compute instances executing in computing resource 222, storage devices provided in computing resource 222, data transfer devices provided by computing resource 222, etc. In some implementations, computing resource 222 may communicate with other computing resources 222 via wired connections, wireless connections, or a combination of wired and wireless connections.

As further shown in FIG. 2, computing resource 222 may include a group of cloud resources, such as one or more applications ("APPs") 222-1, one or more virtual machines ("VMs") 222-2, virtualized storage ("VSs") 222-3, one or more hypervisors ("HYPs") 222-4, or the like.

Application 222-1 may include one or more software applications that may be provided to or accessed by user device 205. Application 222-1 may eliminate a need to install and execute the software applications on user device 205. For example, application 222-1 may include software associated with analytics system 215 and/or any other software capable of being provided via cloud computing environment 220. In some implementations, one application 222-1 may send/receive information to/from one or more other applications 222-1, via virtual machine 222-2.

Virtual machine 222-2 may include a software implementation of a machine (e.g., a computer) that executes programs like a physical machine. Virtual machine 222-2 may be either a system virtual machine or a process virtual machine, depending upon use and degree of correspondence to any real machine by virtual machine 222-2. A system virtual machine may provide a complete system platform that supports execution of a complete operating system ("OS"). A process virtual machine may execute a single program, and may support a single process. In some implementations, virtual machine 222-2 may execute on behalf of a user (e.g., user device 205), and may manage infrastructure of cloud computing environment 220, such as data management, synchronization, or long-duration data transfers.

Virtualized storage 222-3 may include one or more storage systems and/or one or more devices that use virtualization techniques within the storage systems or devices of computing resource 222. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 222-4 may provide hardware virtualization techniques that allow multiple operating systems (e.g., "guest operating systems") to execute concurrently on a host computer, such as computing resource 222. Hypervisor 222-4 may present a virtual operating platform to the guest operating systems, and may manage the execution of the guest operating systems. Multiple instances of a variety of operating systems may share virtualized hardware resources.

Network 225 includes one or more wired and/or wireless networks. For example, network 225 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
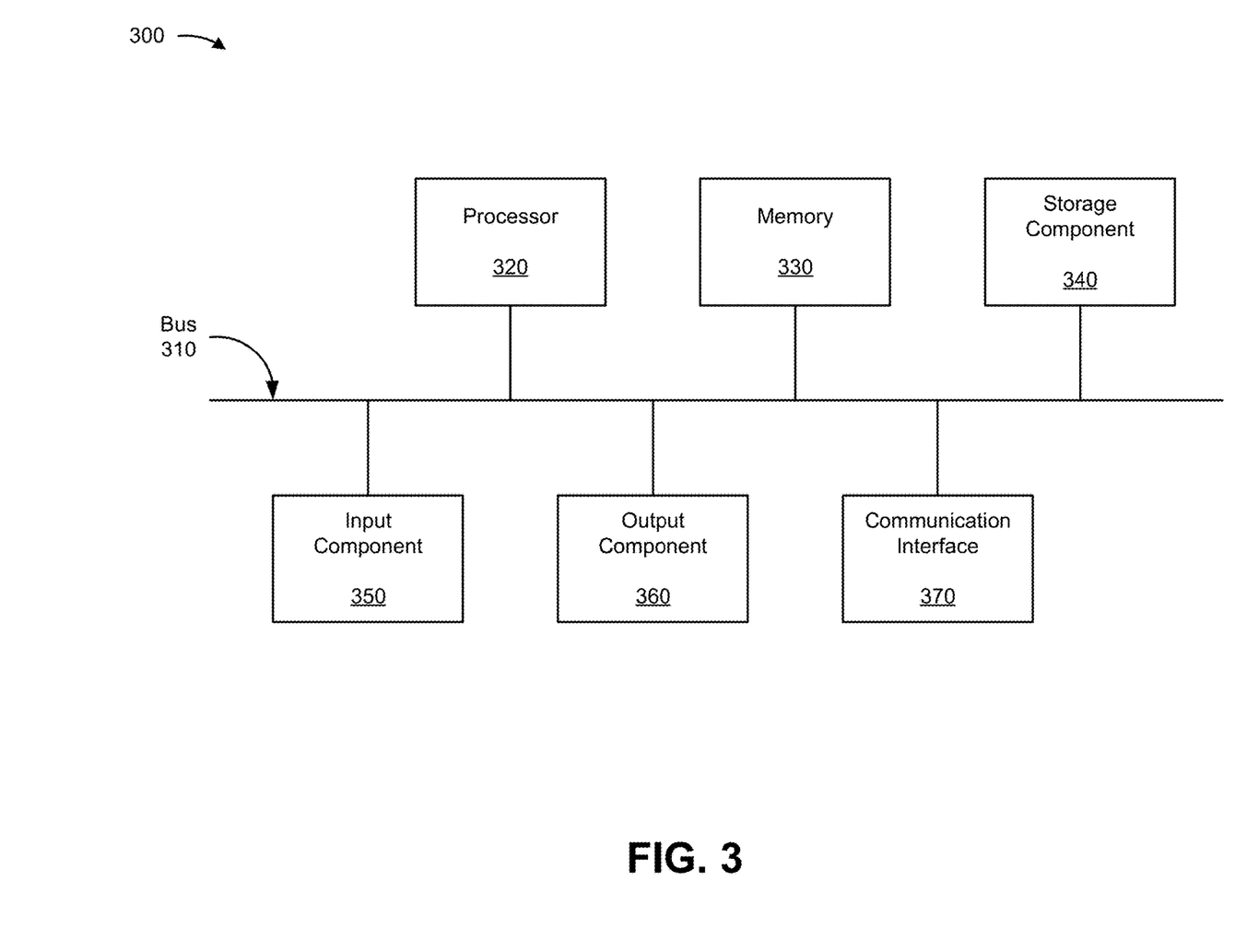
FIG. 3 is a diagram of example components of one or more devices of FIG. 2.

FIG. 3 is a diagram of example components of a device 300. Device 300 may correspond to user device 205, server device 210, and/or analytics system 215. In some implementations, user device 205, server device 210, and/or analytics system 215 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a processor (e.g., a central processing unit (CPU), a graphics processing unit (GPU), and/or an accelerated processing unit (APU)), a microprocessor, a microcontroller, and/or any processing component (e.g., a field-programmable gate array (FPGA) and/or an application-specific integrated circuit (ASIC)) that interprets and/or executes instructions. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
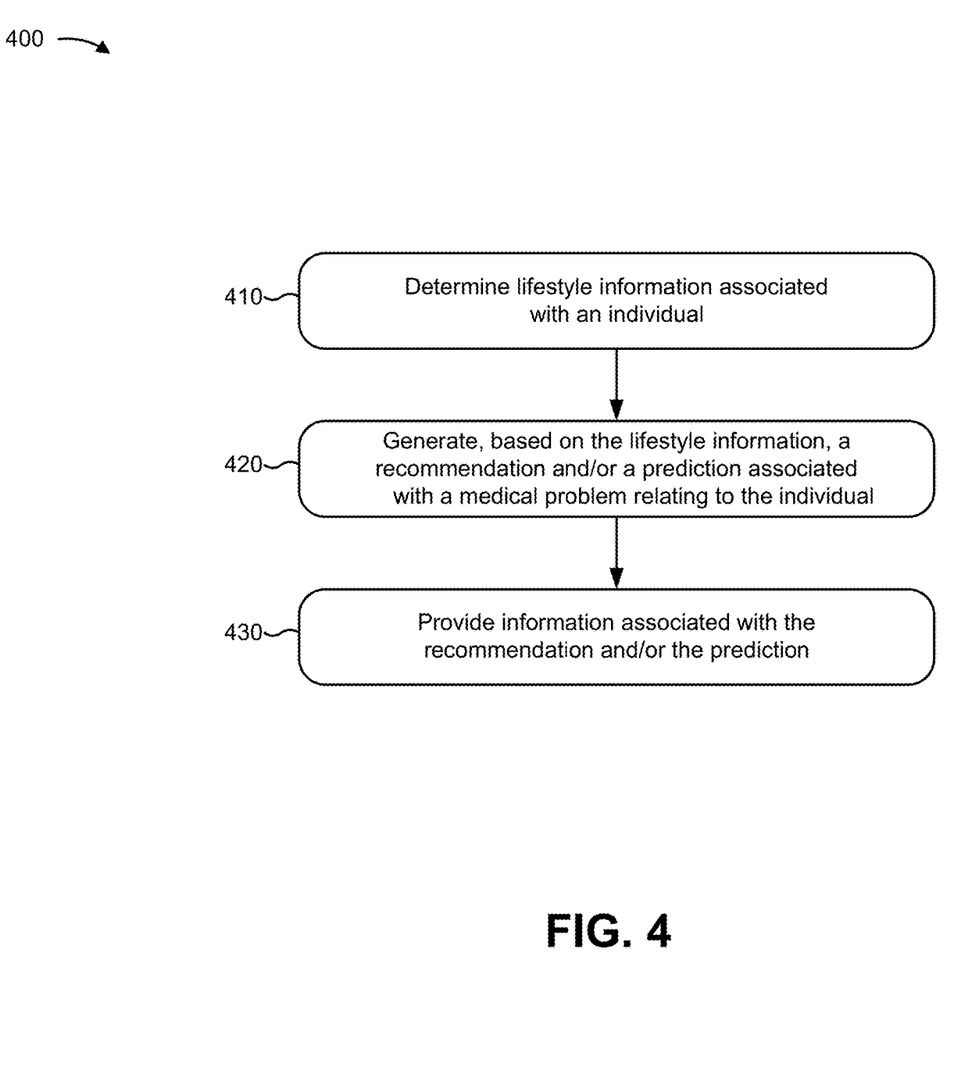
FIG. 4 is a flow chart of an example process for generating a recommendation and/or a prediction, associated with a medical problem relating to an individual, based on lifestyle information associated with the individual.

FIG. 4 is a flow chart of an example process 400 for generating a recommendation and/or a prediction, associated with a medical problem relating to an individual, based on lifestyle information associated with the individual. In some implementations, one or more process blocks of FIG. 4 may be performed by analytics system 215. In some implementations, one or more process blocks of FIG. 4 may be performed by another device or a group of devices separate from or including analytics system 215, such as user device 205 and/or server device 210.

As shown in FIG. 4, process 400 may include determining lifestyle information associated with an individual (block 410). For example, analytics system 215 may receive lifestyle information from user devices 205 and/or server devices 210. In some implementations, the lifestyle information may include information, associated with an individual with a medical problem, that may affect a dosage of a treatment associated with the medical problem. For example, the lifestyle information may include information that may be used to predict or identify a trend in the individual's vital signs and/or other health metrics (e.g., blood glucose levels). Since any of a multitude of factors may affect the medical problem, the various types of lifestyle information (e.g., described below) may be beneficial in that the various types of lifestyle information allow analytics platform 215 to generate a more accurate and/or finely tuned recommendation and/or predication associated with the individual.

As an example, the lifestyle information may include event information associated with the individual, such as a work schedule, a school schedule, a calendar of events, information associated with a school newsletter, or the like.

As another example, the lifestyle information may include sleep information associated with the individual, such as a wake time, a start time of sleep, an amount of movement during sleep, a breathing measurement during sleep, a heart rate during sleep, or the like.

As still another example, the lifestyle information may include activity information associated with the individual, such as information that identifies a type of activity, a duration of the activity, a heart rate during the activity, a blood pressure during the activity, information associated with a period of time of low activity and/or inactivity, or the like.

As yet another example, the lifestyle information may include diet information associated with the individual, such as a type of food or drink consumed by the individual, a quantity of the food or drink consumed by the individual, a time at which the food or drink is consumed by the individual, nutrition information associated with the food or drink (e.g., a quantity of carbohydrates, an amount of protein, an amount of fat, etc.), or the like.

As an additional example, the lifestyle information may include biological information associated with the individual, such as a weight, a height, an age, a gender, a blood pressure, a resting heart rate, a body temperature, a body fat measurement, a blood ketone measurement, a blood glucose measurement, a cholesterol measurement, or the like.

As yet another example, the lifestyle information may include emotional information associated with the individual, such as information indicating whether the individual is experiencing stress, relaxation, happiness, sadness, or the like (i.e., information that identifies an emotional state of the individual at a given time). In some implementations, the emotional information may be obtained based on user input via user device 205 (e.g., input indicating a mood of the individual, a stress level of the individual, etc.). Additionally, or alternatively, the emotional information may be obtained in another manner, such as based on a facial analysis of an image of the individual, determined based on vital signs of the individual, or the like.

As still another example, the lifestyle information may include medical information associated with the individual, such as monitoring information (e.g., information that identifies previous blood glucose levels), dosage information (e.g., information that identifies amounts of previous insulin dosages), times at which previous dosages were administered, or the like.

As another example, the lifestyle information may include location information associated with the individual and/or a location associated with another item of lifestyle information, such as information that identifies a geographic location (e.g., a global positioning system (GPS) location), information indicating whether the individual is indoors or outdoors, information indicating that the individual is at a particular place (e.g., a restaurant, a gym, a park, a movie theater, etc.), information that identifies a location of an event, or the like.

As yet another example, the lifestyle information may include environmental information associated with an environment in which the individual may be present, such as a season (e.g., summer, winter, spring, fall), a phase of the moon, current weather information, forecasted weather information, historical weather information, an air temperature, an atmospheric pressure, air quality information, allergen information, a wind speed, an altitude, a sunrise time, a sunset time, or the like.

As an additional example, the lifestyle information may include transaction information associated with the individual, such as an amount of a transaction (e.g., associated with a credit card, a debit card, etc.), information that identifies items associated with the transaction (e.g., food, drink, movie tickets, park admissions, fitness classes, etc.), information associated with a digital receipt (e.g., stored on a server associated with an application, sent via email, etc.), or the like.

In some implementations, the lifestyle information may be associated with the individual, as described in the above examples. Additionally, or alternatively, the lifestyle information may include general and/or contextual information that is not specific to the individual, such as weather data, geo-spatial information system data, or the like. Here, analytics system 215 may use to add context to one or more other items of lifestyle information. For example, analytics system 215 may use general environmental information (e.g., weather data indicating that it is raining at a particular location) in combination with specific geo-location data (e.g., information that indicates that the individual is at the particular location and information that identifies a speed of movement of the individual) and specific activity information (e.g., indicating a low amount of activity by the individual) in order to determine that the individual is traveling by automobile (e.g., rather than by bicycle or on foot).

In some implementations, the lifestyle information may include timing information (e.g., a time at which food was consumed, a time that a class is to begin, an amount of time that the individual is at a particular location, etc.). In some implementations, analytics system 215 may use the timing information during analysis of the lifestyle information, as described below.

The above types of lifestyle information are provided merely as examples. In some implementations, analytics system 215 may receive additional, other, and/or different types of lifestyle information associated with the individual.

In some implementations, analytics system 215 may receive the lifestyle information from one or more user devices 205. For example, analytics system 215 may receive (e.g., automatically, based on a request, etc.) the lifestyle information from one or more user devices 205 associated with the individual, such as a smart phone, a smart wristwatch, a fitness band, a sensor, a medical device (e.g., an insulin pump, a CGM device, etc.), an accelerometer, or the like. Additionally, or alternatively, analytics system 215 may receive the lifestyle information based on user input (e.g., via one or more user devices) associated with the lifestyle information (e.g., information that is manually entered by the individual).

Additionally, or alternatively, analytics system 215 may receive the lifestyle information from one or more server devices 210, such as one or more application servers associated with applications of user device 205 (e.g., a social media application, a calendar application, a gaming application, an email application, a banking application, a fitness application, a diet tracking application, a camera application, a food planning application, etc.), one or more server devices associated with storing data (e.g., historical weather information, credit card transaction information, nutrition information, fitness information, etc.), or the like.

In some implementations, the lifestyle information may include information identifying previous meals consumed by the individual. For example, analytics system 215 may provide, for display to the individual, a set of images associated with one or more previous servings of a meal and/or portions of the items included in the meal, where each image may include a size reference indicator (e.g., such that the individual may readily identify a portion size of items included in the meal). Here, the individual may select an image that represents the portion sizes of the current meal. Alternatively, the individual may decide not to select an image (e.g., such that the predicted portion sizes are unchanged). In some implementations, analytics system 215 may prompt the individual to capture an image (e.g., via a user device), such that analytics system 215 may store the image for future use and/or prediction.

In some implementations, the lifestyle information may be historical (e.g., associated with a previous physical activity, a previous meal, an earlier event, etc.), current lifestyle information (e.g., associated with an ongoing physical activity, a current heart rate, a current weight, a current value associated with a health metric related to the medical problem, etc.), and/or future lifestyle information (e.g., associated with a planned event, an upcoming meal, etc.).

In some implementations, analytics system 215 may store or have access to predetermined information that may be used to augment and/or supplement the lifestyle information. For example, analytics system 215 may store or have access to nutrition information associated with one or more types of food or drink (e.g., such that analytics system 215 may calculate blood glucose based on the nutrition information rather than relying on the individual to input the nutrition information).

As further shown in FIG. 4, process 400 may include generating, based on the lifestyle information, a recommendation and/or a prediction associated with a medical problem relating to the individual (block 420). For example, analytics system 215 may generate the recommendation and/or the prediction. In some implementations, the recommendation may include a recommendation associated with a dosage of treatment associated with managing the medical problem (e.g., dosage of insulin, food, beverages, supplements, and/or other medications to manage diabetes). In some implementations, the recommendation may include a dosage, a time to administer a dosage, a predicted pre-dosage metric (e.g., a predicted pre-insulin blood glucose level), a predicted post-dosage metric (e.g., a predicted post-insulin blood glucose level), a type of medicine (e.g., rapid-acting insulin, short-acting insulin, long-acting insulin, 70/30 insulin, 50/50 insulin), a brand of medicine, or the like. In some implementations, the recommendation may include a glucose dosage recommendation which may include a recommendation to consume certain foods, beverages, supplements, etc. (e.g., in the case of hypoglycemia in which foods, beverages, glucose supplements, and/or medications, such as glucagon, may be needed to elevate the individual's blood glucose levels).

In some implementations, the recommendation for a dosage of a treatment may include information identifying an immediate dosage, a dosage at a future time, a dosage in anticipation of a future physical activity identified by the lifestyle information, or the like, and/or a prediction associated with the medical problem. For example, in the case of a diabetic individual, analytics system 215 may analyze the lifestyle information associated with the individual, may determine, based on analyzing the lifestyle information, a recommendation for an insulin dosage or glucose dosage in anticipation of an upcoming activity. Analytics system 215 may also determine a predicted change in a blood glucose level associated with the recommended insulin dosage or glucose dosage. In some implementations, the recommendation may include a prediction, a forecast, an estimate, or the like, associated with the medical problem (e.g., predicted blood glucose levels during a future time or future time window) such that the individual is informed regarding managing the medical problem at the future time or future time window.

As described herein, analytics system 215 may generate the prediction by converting (e.g., merging, combining, normalizing) the lifestyle information such that items of the lifestyle information are in a format that can be used to create a lifestyle timeline associated with the individual (i.e., analytics system 215 may create converted lifestyle information based on merging, combining, and/or normalizing the lifestyle information). In some implementations, the lifestyle timeline may include a series (e.g., multiple) of items of lifestyle information (e.g., events, activities, meals, sleep) arranged in a chronological order. For example, the lifestyle timeline may include historical items of lifestyle information, current items of lifestyle information, and/or future items of lifestyle information (e.g., events, activities, meals, sleep) arranged in a chronological order. In other words, the lifestyle timeline may include a combination of historical items of lifestyle information, current items of lifestyle information, and/or future items of lifestyle information.

In some implementations, analytics system 215 may determine one or more predictive factors associated with the medical problem (e.g., a factor and/or amount by which a metric, relating to the medical problem, may be affected by an item of lifestyle information). For example, the predictive factor may be a factor and/or an amount by which ingestion of a particular food item will affect a blood glucose level. As another example, the predictive factor may include a factor and/or an amount by which a period of sleep will affect a blood glucose level. As another example, the predictive factor may include a factor and/or an amount by which a period of certain activity (e.g., exercise, walking, running, and/or another activity) will affect a blood glucose level. As another example, the predictive factor may include a factor and/or an amount by which medication will affect a blood glucose level.

In some implementations, the predictive factor may vary from individual to individual. For example, the predictive factor may be determined based on previous lifestyle information (e.g., the previous effect of certain activity on the individual's blood glucose level). Additionally, or alternatively, the predictive factor may be based on an item of lifestyle information (e.g., a known effect of a particular food item or medication on the individual's blood glucose level). Additionally, or alternatively, the predictive factor may be based on both information associated with the individual (e.g., weight) and the item of lifestyle information (e.g., a known effect of ingesting an apple may be modified based on the weight). In some implementations, different predictive factors may be determined for different items of lifestyle information (e.g., one predictive factor may be determined for a particular food item and another predictive factor may be determined for a particular activity).

Analytics system 215 may generate the prediction based on the predictive factors and the timeline. In other words, analytics system 215 may determine an effect of the lifestyle information on the medical problem using the predictive factors. Additionally, or alternatively, analytics system 215 may analyze the lifestyle information to identify patterns, correlations, trends, or the like, associated with the individual, and may generate the recommendation and/or the prediction based on the identified patterns, correlations, trends, or the like. As an example, analytics system 215 may identify a trend in the individual's glucose levels based on the individual's consumption of certain foods. For example, analytics system 215 may identify the trend based on information identifying the previous effects of the foods on the individual's blood glucose levels. Additionally, or alternatively, the trend may be based on the predictive factor. As another example, analytics system 215 may identify a trend in the individual's glucose levels based on the individual's activities (e.g., based on information identifying the previous effects of the activities on the individual's blood glucose levels and/or based on the predictive factor associated with the activities).

Additionally, or alternatively, analytics system 215 may generate a state associated with the individual. The state associated with the individual may include information such as sums, averages, minimums, or maximums of parameters associated with managing or monitoring the medical problem, such as insulin, glucose, carbohydrates, sleep, or the like, in the case of the diabetic individual. The state may also include other information, such as changes in values associated with one or more items of lifestyle information, ratios, moving averages, counts, or the like. Additionally, or alternatively, analytics system 215 may apply one or more other analytics techniques.

In some implementations, analytics system 215 may use a nearest neighbor analysis to generate the recommendation and/or the prediction. For example, analytics system 215 may identify a current state and one or more historical states (e.g., historical instances of similar states, states that match the current state within a threshold, or the like), identify historical recommendations, historical predictions and outcomes associated with the one or more historical states, and generate the recommendation based on the historical recommendations and outcomes (e.g., such that recommendations and/or predictions that resulted in positive outcomes may be repeated). In some implementations, the nearest neighbor of the nearest neighbor analysis can be nearest in state, nearest in time, a combination thereof, or the like.

In some implementations, analytics system 215 may store or have access to a prediction model associated with predicting and/or forecasting the recommended dosage of the treatment. For example, analytics system 215 may receive historical lifestyle information associated with the individual and/or one or more other individuals, and may create a prediction model associated with predicting and/or forecasting the recommended dosage of the treatment and/or a prediction associated with the medial problem (e.g., a predicted trend of blood glucose levels). In some implementations, analytics system 215 may create the model and may implement one or more analytic techniques, such as regression, uplift modeling, forecasting, neural networks, random forests, or the like. In this example, analytics system 215 may provide lifestyle information (e.g., received at a later time) as an input to the prediction model, and may receive, as an output, the predicted recommended dosage of the treatment and/or a prediction associated with the medical problem. For example, as described herein, the prediction and/or the recommended dosage of the treatment may be based on lifestyle information that identifies a trend in a metric (e.g., a trend of blood glucose levels based on the effect of the individual's activity, foods consumed, etc.) and the effect of treatment on the metric (e.g., the effect of medicine and/or glucose consumption on the individual's blood glucose levels).

In some implementations, analytics system 215 may train and/or update the prediction model (e.g., based on additional lifestyle information received at a later time). Additionally, or alternatively, analytics system 215 may train and/or update the prediction model based on user input. For example, analytics system 215 may update the prediction model based on actual dosage information, associated with an actual dosage of treatment administered by the individual, after a recommendation and/or a prediction is provided by analytics system 215.

As further shown in FIG. 4, process 400 may include providing information associated with the recommendation and/or the prediction (block 430). For example, analytics system 215 may provide the information associated with the recommendation and/or the prediction to one or more user devices 205. In some implementations, analytics system 215 may provide information associated with the recommendation (e.g., a recommended dosage, a recommended time to administer the dosage, or the like). In some implementations, analytics system 215 may provide information associated with the prediction (e.g., a predicted time at which a blood glucose level will satisfy a threshold, a predicted blood glucose level at a particular time, or the like).

In some implementations, analytics system 215 may provide, for display, one or more user interfaces associated with the recommendation and/or the prediction. For example, in addition to providing, for display, information associated with the recommended dosage, analytics system 215 may provide one or more user interfaces (e.g., graphs, charts, lists, images, etc.) associated with activity information associated with the individual, medical information associated with the individual (e.g., blood glucose levels of the individual), sleep pattern information associated with the individual, diet information associated with the individual, or the like.

In some implementations, analytics system 215 may provide, for display, information associated with one or more items of lifestyle information that were used to generate the recommendation. In such a case, the user may update (e.g., modify, edit, correct, or the like) the one or more items of lifestyle information. Here, analytics system 215 may receive, from user device 205, the updated lifestyle information, update the lifestyle timeline, and update the recommendation or the prediction, accordingly (e.g., based on the updated lifestyle information and/or the updated lifestyle timeline). Analytics system 215 may provide the updated recommendation and/or the updated prediction to allow the individual to make a judgment regarding monitoring and/or managing the medical problem (e.g., rather than a diagnosis or a prescription). In some implementations, the user may provide information identifying the treatment used to manage the medical problem to analytics system 215, and analytics system 215 may store this information for future use (e.g., to determine trends in blood glucose levels at a future time). For example, the user may indicate, via user device 205, that the user injected a particular amount of insulin or consumed a particular amount of glucose based on receiving the recommendation.

As a particular example of how analytics system 215 may operate, assume that analytics system 215 is to provide a recommended treatment dosage to an individual with diabetes (e.g., a dosage of insulin and/or a dosage of glucose). In this case, analytics system 215 may receive (e.g., from a server associated with a calendar application) school schedule information associated with the individual, and may receive (e.g., from a fitness band worn by the individual) historical physical activity information (e.g., for a most recent week, a most recent month, etc.) indicating that the individual will either walk to school or bike to school. Here, analytics system 215 may combine weather information (e.g., received from a server associated with a weather application), and predict (e.g., for an upcoming day) whether the individual will walk to school or bike to school. Analytics system 215 may then combine sleep information (e.g., received from a sensor worn by the individual) with the walk or bike prediction, and recommend an amount insulin to be administered to the individual for the upcoming predicted physical activity (e.g., the walk or the bike ride) and/or predict a change in a blood glucose level associated with the upcoming predicted physical activity.

As another example associated with recommending an insulin dosage, analytics system 215 may pair location information, associated with the individual, with transaction information associated with a credit card of the individual. In one example case, analytics system 215 may determine that the individual may be not be physically active for a period of time (e.g., while watching a movie at a movie theater), and may identify food that will be ingested during the non-active period of time, (e.g., by identifying a purchase of popcorn at the movie theater). Here, analytics system 215 may, based on the location information and the transaction information, predict a change in a blood glucose level and may determine a recommended amount insulin to the individual, and provide the prediction and/or the recommendation accordingly. More specifically, analytics system 215 may predict a change in a blood glucose level and may determine a recommended amount of insulin to the individual based on the activity of the individual and the food consumed by the user.

As another example of how analytics system 215 may operate, again assume that analytics system 215 is to provide a recommended dosage of insulin to an individual with diabetes. In this example, assume that analytics system 215 has provided a recommended dosage of insulin for an individual that is sitting down to eat a meal (e.g., a school lunch). In this case, analytics system 215 may have determined the recommended dosage of insulin based on lifestyle information including predicted physical activities in the near future (e.g., after the meal) and predicted nutrition information associated with the meal, such as a quantity of carbohydrates, an amount of fat, or the like.

In some implementations, the individual may provide information regarding the meal (e.g., ingredients, portion sizes, etc.), and analytics system 215 may obtain nutritional information regarding the meal. Further, analytics system 215 may determine a trend in the individual's blood glucose levels based on the consumption of the meal, recent activities, and/or future activities. As described above, the future activities may be predicted based on the individual's schedule information. Additionally, or alternatively, the individual may manually enter future activities.

In some implementations, analytics system 215 may determine that the individual did not participate in a predicted future activity (e.g., an exercise session) based on the individual's vital signs (e.g., heart rate) obtained from a fitness band. Additionally, or alternatively, analytics system 215 may determine that the individual did not participate in a predicted future activity (e.g., attending of a class) based on the individual's location. Analytics system 215 may update predictions and/or recommendations based on determining that the individual did not participate in a predicted future activity.

In some implementations, analytics system 215 may cause an action to be automatically performed based on providing the information associated with the recommendation and/or the prediction. For example, the recommendation regarding dosage may be automatically provided to an insulin pump, and the individual may accept, modify, or cancel the recommendation via a user interface of the insulin pump. In some implementations, recommendation regarding dosage may include a basil rate, bolus, and/or other information that an insulin pump may use to adjust the dosage of insulin being provided to the individual.

As another example, analytics system 215 may provide the information associated with the recommendation and/or the prediction in order to cause a notification (e.g., an alarm, a vibration, a shock, a message) to be automatically provided by user device 205. As a particular example, analytics platform 215 may cause an alarm to be set on user device 205, where the alarm may be configured to make an audible sound and/or provide (e.g., via a display screen) the information associated with the recommendation and/or the prediction prior to (e.g., 15 minutes before) and/or at a time that the individual's blood glucose level is predicted to reach a threshold.

As yet another example, analytics platform 215 may provide the information associated with the recommendation and/or the prediction in order to cause a current reading, of the health metric to be collected and/or provided for display to the individual (e.g., such that the current reading is provided to the individual along with the recommendation and/or the prediction).

In some implementations, the lifestyle information and/or the information associated with the recommendation and/or the prediction may be encrypted for transmission to and/or from user device 205, server device 210, and/or analytics platform 215 (e.g., in order to protect privacy of the individual).

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Implementations described herein may provide a monitoring and treatment dosage prediction system that is capable of determining lifestyle information associated with an individual. Further, implementations described herein may analyze the lifestyle information (e.g., to identify patterns, correlations, trends, etc.) associated with the individual, and provide the individual with a recommended dosage of the treatment (e.g., an immediate dosage of the treatment, a future dosage of the treatment, etc.). Additionally, or alternatively, implementations described herein may predict other conditions associated with the medical problem (e.g., a predicted change or trend in a blood glucose level).

In this way, processing resources, memory resources, and/or battery life of user device 205 may be conserved (e.g., since user device 205 is not required to store the lifestyle information, analyze the lifestyle information, create the lifestyle timeline, and/or generate the recommendation and/or prediction.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:
1. A method, comprising:
receiving, by a device and from at least one of a sensor of a user device or a server device via a network, lifestyle information corresponding to a user, of the user device, with a medical condition;
creating, by the device and based on receiving the lifestyle information, a lifestyle timeline associated with the user,
the lifestyle timeline:
including a plurality of items of lifestyle information, included in the lifestyle information, and having the plurality of items of lifestyle information arranged in a chronological order;
generating, by the device and based on receiving the lifestyle timeline, a recommendation or a prediction associated with a metric related to the medical condition,
the recommendation being generated based on one or more of the plurality of items of lifestyle information, or
the prediction being generated using a prediction model that uses one or more of the plurality of items of lifestyle information as input;
receiving, by the device and from another device via the network, transaction information associated with a purchase of food by the user;
receiving, by the device via the network, location information associated with the user;
generating, by the device and based on the transaction information and the location information, an updated recommendation regarding insulin dosage; and providing, by the device and to an insulin device via the network, the updated recommendation,
upon receipt of the updated recommendation, the insulin device adjusting an amount of insulin to a recommended dosage identified by the updated recommendation after the updated recommendation is accepted via a user interface of the insulin device, and
the insulin device administering the amount of insulin to the user after the updated recommendation is accepted via the user interface of the insulin device.

2. The method of claim 1, further comprising:
determining a set of predictive factors associated with the medical condition,
a predictive factor, of the set of predictive factors, being a factor or an amount by which the metric is predicted to be affected by an item of lifestyle information of the plurality of items of lifestyle information; and
where generating the recommendation or the prediction associated with the metric comprises:
generating the recommendation or the prediction based on the set of predictive factors.

3. The method of claim 1, where the plurality of items of lifestyle information includes a combination of historical items of lifestyle information, current items of lifestyle information, and future items of lifestyle information.

4. The method of claim 1, where receiving the lifestyle information comprises:
receiving the lifestyle information based on user input via the user device.

5. The method of claim 1, where receiving the lifestyle information comprises:
automatically receiving the lifestyle information from the user device.

6. A device, comprising:
a memory; and
one or more processors to:
receive, from at least one of a sensor of a user device or a server device via a network, lifestyle information corresponding to a user, of the user device, with a medical problem;
create, based on receiving the lifestyle information, a lifestyle timeline associated with the user,
the lifestyle timeline:
including a plurality of items of lifestyle information included in the lifestyle information, and having the plurality of items of lifestyle information arranged in a chronological order;
generate, based on receiving the lifestyle timeline, a recommendation or a prediction associated with a health metric related to the medical problem,
the recommendation including a recommended dosage of a treatment associated with the health metric and being generated based on one or more of the plurality of items of lifestyle information, or
the prediction including a predicted value of the health metric at a future time and being generated by a prediction model that uses one or more items of the plurality of items of lifestyle information as input;
receive, from another device via the network, transaction information associated with a purchase of food by the user;
receive, via the network, location information associated with the user;
generate, based on the transaction information and the location information, an updated recommendation regarding insulin dosage; and provide, to an insulin device via the network, the updated recommendation,
upon receipt of the updated recommendation, the insulin device adjusting an amount of insulin to a recommended dosage identified by the updated recommendation after the updated recommendation is accepted via a user interface of the insulin device, and
the insulin device administering the amount of insulin to the user after the updated recommendation is accepted via the user interface of the insulin device.

7. The device of claim 6, where the one or more processors are further to:
determine, based on the lifestyle timeline, a current state associated with the user; and
identify, using a nearest neighbor analysis, a historical state similar to the current state; and
where the one or more processors, when generating the recommendation or the prediction, are to:
generate the recommendation or the prediction based on a historical recommendation or a historical prediction corresponding to the historical state.

8. The device of claim 6, where the one or more processors, when receiving the lifestyle information, are to:
receive the lifestyle information from the server device, the server device having access to the lifestyle information.

9. The device of claim 6, where the one or more processors are further to: merge, combine, or normalize the lifestyle information to create converted lifestyle information,
the converted lifestyle information being formatted to permit creation of the lifestyle timeline; and
where the one or more processors, when creating the lifestyle timeline, are to: create the lifestyle timeline based on the converted lifestyle information.

10. The device of claim 6, where the one or more processors are further to:
determine, based on the lifestyle information, a current value associated with the health metric; and
where the one or more processors, when generating the recommendation or the prediction, are to:
generate the recommendation or the prediction based on the current value of the health metric.

11. The device of claim 6, where the one or more processors, when receiving the lifestyle information, are to:
receive the lifestyle information from the user device,
the user device being a device that is worn by the user.

12. The device of claim 6, where the lifestyle information includes at least one of:
event information from a schedule or calendar associated with the user;
sleep information associated with the user;
information associated with an activity in which the user has participated, is participating in, or is to participate;
information associated with a diet of the user;
biological information associated with the user;
information associated with an emotional state of the user;
medical information, associated with treating the medical problem, corresponding to the user;
information associated with a location of the user;
environmental information associated with the user; or
information associated with one or more transactions associated with the user.

13. A non-transitory computer-readable medium storing instructions, the instructions comprising:
one or more instructions that, when executed by one or more processors, cause the one or more processors to:

receive, from at least one of a sensor of a user device or a server device via a network, lifestyle information corresponding to a user, of the user device, with a medical problem;

create, based on receiving the lifestyle information, a lifestyle timeline associated with the user, the lifestyle timeline:

including a plurality of items of lifestyle information included in the lifestyle information, and having the plurality of items of lifestyle information arranged in a chronological order;

determine, based on receiving the lifestyle information, a current value of a metric associated with the medical problem;

generate, based on receiving the lifestyle timeline and the current value of the metric, a recommendation or a prediction associated with the metric, the recommendation being generated based on a first set of the plurality of items of lifestyle information, or the prediction being generated using a predictive model that uses a second set of the plurality of items of lifestyle information as input;

receive, from another device via the network, transaction information associated with a purchase of food by the user;

receive, via the network, location information associated with the user;

generate, based on the transaction information and the location information an updated recommendation regarding an insulin dosage; and provide, to an insulin device via the network, the updated recommendation, upon receipt of the updated recommendation, the insulin device adjusting an amount of insulin to a recommended dosage identified by the updated recommendation after the updated recommendation is accepted via a user interface of the insulin device, and the insulin device administering the amount of insulin to the user after the updated recommendation is accepted via the user interface of the insulin device.

14. The non-transitory computer-readable medium of claim 13, where the one or more instructions, when executed by the one or more processors, further cause the one or more processors to:

receive updated lifestyle information corresponding to the user, the updated lifestyle information being different from the lifestyle information; and update the lifestyle timeline, based on the updated lifestyle information, to create an updated lifestyle timeline; and where the one or more instructions, that cause the one or more processors to generate the updated recommendation, cause the one or more processors to:

generate, based on the updated lifestyle timeline, the updated recommendation.

15. The non-transitory computer-readable medium of claim 13, where the one or more instructions, when executed by the one or more processors, further cause the one or more processors to:

determine a set of predictive factors associated with the medical problem, a predictive factor, of the set of predictive factors, being a factor or an amount by which the metric is predicted to be affected by an item of lifestyle information of the plurality of items of lifestyle information; and where the one or more instructions, that cause the one or more processors to generate the recommendation or the prediction, cause the one or more processors to:

generate the recommendation or the prediction further based on the set of predictive factors.

16. The non-transitory computer-readable medium of claim 13, where the updated recommendation identifies a recommended time at which the recommended dosage should be administered.

17. The non-transitory computer-readable medium of claim 13, where the plurality of items of lifestyle information includes at least two of:

historical items of lifestyle information;

current items of lifestyle information; or future items of lifestyle information.

18. The method of claim 1, where the location information includes at least one of:

information that identifies a geographic location of the user, information indicating whether the user is indoors or outdoors, or information indicating that the user is at a particular place.

19. The method of claim 1, where a notification is provided by the user device based on the updated recommendation.

20. The non-transitory computer-readable medium of claim 13, where the transaction information includes at least one of:

an amount of a transaction, information that identifies items associated with the transaction, or information associated with a digital receipt.

* * * * *